United States Patent
Kurek et al.

(10) Patent No.: US 6,395,943 B1
(45) Date of Patent: *May 28, 2002

(54) PROCESS FOR INHIBITING THE POLYMERIZATION OF VINYL AROMATIC COMPOUNDS

(75) Inventors: Paul R. Kurek, Barrington; Robert R. Frame, Glenview, both of IL (US)

(73) Assignee: UOP LLC, Des Plaines, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/371,455

(22) Filed: Aug. 10, 1999

(51) Int. Cl.$^7$ .................................................. C07C 7/20
(52) U.S. Cl. ......................... 585/5; 585/832; 585/4; 208/2; 208/48 AA; 208/348; 208/349
(58) Field of Search ................. 585/4, 5, 832; 208/2, 48 AA, 348, 349

(56) References Cited

U.S. PATENT DOCUMENTS

| | | | |
|---|---|---|---|
| 3,988,212 A | 10/1976 | Watson | 203/209 |
| 4,013,580 A | 3/1977 | Hayashi et al. | 252/182 |
| 4,050,993 A | 9/1977 | Daniels | 203/209 |
| 4,341,600 A | 7/1982 | Watson | 203/209 |
| 4,466,905 A * | 8/1984 | Butler et al. | 252/403 |
| 4,654,451 A | 3/1987 | Miller et al. | 585/585 |
| 4,774,374 A * | 9/1988 | Abruscato et al. | 585/24 |
| 4,863,587 A * | 9/1989 | Tonari et al. | 208/263 |
| 4,929,778 A | 5/1990 | Roling | 585/583 |
| 4,967,027 A | 10/1990 | Takahashi et al. | 585/585 |
| 4,973,787 A * | 11/1990 | Colvin | 585/508 |
| 4,982,034 A * | 1/1991 | Moore et al. | 585/435 |
| 5,034,156 A | 7/1991 | Varwig | 252/403 |
| 5,254,760 A | 10/1993 | Winter et al. | 585/585 |
| 5,312,952 A | 5/1994 | Grossi et al. | 558/546 |
| 5,396,004 A | 3/1995 | Arhancet et al. | 585/585 |
| 5,396,005 A * | 3/1995 | Arhancet | 585/5 |
| 5,446,220 A * | 8/1995 | Arhancet | 585/5 |
| 5,773,674 A * | 6/1998 | Arhancet et al. | 585/5 |
| 5,869,717 A * | 2/1999 | Frame et al. | 585/5 |
| 6,117,276 A * | 9/2000 | Cunkle et al. | 203/8 |

FOREIGN PATENT DOCUMENTS

| | | |
|---|---|---|
| EP | 697 386 A1 | 7/1995 |
| JP | J59029624 A | 8/1982 |
| JP | JO1226858 A | 9/1989 |
| JP | JO3149205 A | 6/1991 |
| JP | 05310815 A | 11/1993 |
| JP | 07010910 A | 1/1995 |
| WO | WO95/03263 | 2/1995 |

* cited by examiner

*Primary Examiner*—Bekir L. Yildirim
(74) *Attorney, Agent, or Firm*—John G. Tolomei; Frank B. Molinaro

(57) ABSTRACT

A process is disclosed for inhibiting the polymerization of vinyl aromatic compounds, such as styrene, during its distillation. The process involves adding a mixture of at least two inhibitors to the vinyl aromatic compound. One such combination is N,N'-di-2-butyl-N,N',4-dinitroso-1,4-diaminobenzene and dinitrocresol. A stabilizer such as N,N'-di-2-butyl-1,4-diaminobenzene can also be added.

18 Claims, No Drawings

PROCESS FOR INHIBITING THE POLYMERIZATION OF VINYL AROMATIC COMPOUNDS

FIELD OF THE INVENTION

This invention relates to a process for inhibiting the polymerization of vinyl aromatic compounds such as styrene during its distillation. The process involves adding to the vinyl aromatic compound a mixture of at least one nitroso compound such as N,N'-di-2-butyl-N,N'-dinitroso-1,4-diaminobenzene and a dinitrophenol compound such as dinitrocresol, and optionally a stabilizer compound such as an N,N'-dialkyl substituted 1,4-diaminobenzene.

BACKGROUND OF THE INVENTION

Styrene is one of several vinyl aromatic compounds which has considerable commercial utility. Styrene is polymerized into polystyrene which is a clear, readily colored and easily fabricated plastic with many uses. The efficiency of the polymerization process is dependent on the purity of the monomer starting material. Since the processes for producing styrene, and other vinyl aromatic compounds, will contain various reaction products including benzene, toluene, etc., the mixture is distilled to separate these undesirable contaminants. Unfortunately, the temperatures required for distillation, typically 90° C. to about 150° C., leads to the polymerization of the vinyl aromatic compounds. In order to minimize or prevent polymerization of the vinyl aromatic monomer, it is common to add a polymerization inhibitor to the distillation mixture.

The art discloses a variety of compounds which are claimed to inhibit polymerization. These include U.S. Pat. No. 4,050,993, which discloses the use of N,N-dinitrosomethylaniline as a polymerization inhibitor. U.S. Pat. No. 3,988,212, which disclose the use of N-nitrosodiphenyl amine in combination with dinitro-o-cresol. U.S. Pat. No. 4,013,580, which discloses the use of N-nitroso aniline derivatives. U.S. Pat. No. 4,941,800, which discloses the use of a mixture of dinitro-p-cresol and N-nitroso-diphenyl amine. U.S. Pat. No. 4,654,451, which discloses alkyl substituted p-nitroso phenols in combination with p-nitroso phenol. U.S. Pat. No. 5,034,156 which discloses N-nitrosophenyl-hydroxylamine plus hydroquinone monomethyl ether. U.S. Pat. No. 5,396,004, which discloses a phenylenediamine compound plus a hydroxyalkylhydroxyl-amine compound. U.S. Pat. No. 5,254,760, which discloses 1-oxyl-2,2,6,6-tetramethylpiperidine plus an aromatic nitro compound. U.S. Pat. No. 4,929,778, which discloses a phenylenediamine compound plus a hindered phenol compound. U.S. Pat. No. 5,312,952, which discloses the use of the reaction product of a $C_9$–$C_{20}$ alkyl phenol with sulfuric and nitric acid and, optionally, an aryl or alkyl-substituted phenylenediamine. WO9503263, which discloses 3,5-di-tert-butyl-4-hydroxy-N,N-dimethyl benzyl amine. EP-697386-A2, which discloses 4-acetylamino-2,2,6,6-tetramethyl piperidine N-oxyl in combination with 4-nitroso phenol. JP0701910-A, which discloses phosphite compounds, nitrosoamine compounds or phenol compounds. JP05310815-A, which discloses the ammonium salt of N-nitrosophenyl hydroxylamine. JP03149205-A, which discloses nitrosophenols plus dicyclohexylammonium nitrate. J01226858-A, which discloses the use of substituted nitrosobenzene. U.S. Pat. No. 4,967,027, which discloses p-nitroso phenol plus p-t-butyl catechol. J59029624-A, which discloses the use of N-nitroso compound, e.g., N-nitroso-diphenylamine and a catechol, e.g., p-t-butylcatechol.

Finally, U.S. Pat. No. 5,869,717, discloses the use of N-nitroso derivatives of unsubstituted or dialkyl substituted phenylenediamine.

Applicants have now discovered that N-nitroso derivatives of unsubstituted or dialkyl substituted phenylenediamine (diaminobenzene) can be combined with unsubstituted or alkyl substituted dinitrophenolic compounds.

SUMMARY OF THE INVENTION

As stated, this invention relates to a process for inhibiting the polymerization of a vinyl aromatic compound during its distillation. One embodiment of the process involves adding to the vinyl aromatic compound an effective amount of a mixture of: 1) a nitroso compound selected from the group consisting of

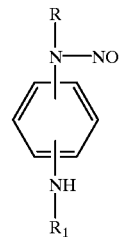

(I)

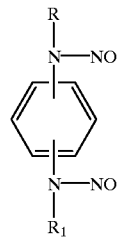

(II)

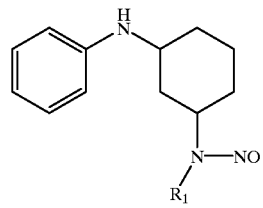

(III)

and mixtures thereof, where R and $R_1$ are each independently hydrogen, cyclohexyl, phenyl or an alkyl group having from 1 to 18 carbon atoms and 2) a nitrophenol compound selected from the group consisting of dinitrocresol, dinitrophenol, 2-sec-butyl-4,6-dinitrophenol, and mixtures thereof.

Another embodiment of the invention is a process for inhibiting the polymerization of a vinyl aromatic compound comprising adding to the compound an effective amount of a mixture of: 1) a nitroso compound selected from the group consisting of

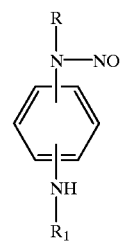 (I)

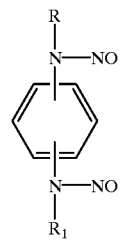 (II)

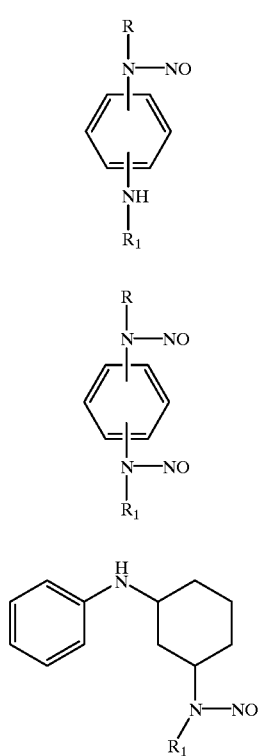 (III)

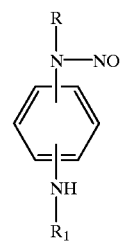 (I)

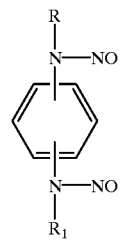 (II)

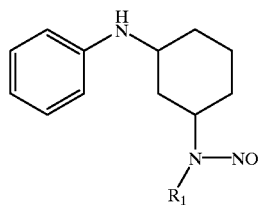 (III)

and mixtures thereof, where R and $R_1$ are each independently hydrogen, cyclohexyl, phenyl or an alkyl group having from 1 to 18 carbon atoms; 2) a nitrophenol compound selected from the group consisting of dinitrocresol, dinitrophenol, 2-sec-butyl-4,6-dinitrophenol and $C_1$ to $C_{18}$ alkyl substituted nitrophenols and mixtures of, and 3) a stabilizer selected from the group consisting of phenylenediamine, dihydroxy phenol, diphenylamine, alkyl substituted phenylenediamines, phenol, $C_1$ to $C_{18}$ alkyl substituted phenols and mixtures thereof.

These and other objects and embodiments will become more evident after a detailed description of the invention.

DETAILED DESCRIPTION OF THE INVENTION

The present invention relates to a process for inhibiting the polymerization of a vinyl aromatic compound during its distillation. Vinyl aromatic compounds to which the instant process is applicable include styrene, alpha-methyl styrene, divinylbenzene, vinyl toluene, vinyl naphthalene and polyvinyl-benzene In most cases this process will be practiced during distillation wherein air is not present. Anaerobic conditions are desired to stabilize vinyl aromatic compounds (inhibit polymerization). These conditions require the special inhibitors of the current invention.

The process generally involves adding a mixture of at least two inhibitor compounds to the vinyl aromatic compound during its distillation. One inhibitor is selected from the group consisting of 1) a nitroso compound selected from the group consisting of and mixtures thereof, where R and $R_1$ are each independently hydrogen, cyclohexyl, phenyl or an alkyl group having from 1 to 18 carbon atoms; 2) a nitrophenol compound preferably selected from the group consisting of dinitrocresol, dinitrophenol, 2-sec-butyl-4,6-dinitrophenol and $C_1$ to $C_{18}$ alkyl substituted nitrophenols and mixtures thereof, and 3) a stabilizer selected from the group consisting of phenylenediamine (1,4-diaminobenzene), dihydroxy phenol, diphenylamine, alkyl substituted phenylenediamines, phenols, $C_1$ to $C_{18}$ alkyl substituted phenols and mixtures thereof.

In structures I and II, the R and $R_1$ groups can each independently be hydrogen, cyclohexyl, phenyl or an alkyl group having from 1 to 18 carbon atoms. Illustrative of the alkyl groups which can be used are methyl, ethyl, propyl, butyl, pentyl, octyl, decyl, sec-butyl, iso-propyl, cyclohexane and isopentyl. Included in structures I and II above are the o, m and p isomers. Preferred compounds encompassed within structure I and II are the following compounds having structure IA and IIA.

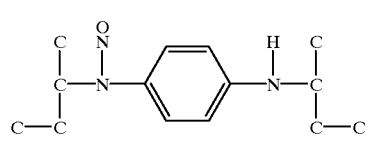 (IA)

N,N'-di-2-butyl-N-nitroso-1,4 diaminobenzene (IIA)

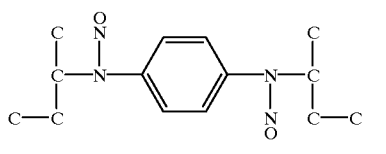

N,N'-di-2-butyl-N, N'-dinitroso-1,4 diaminobenzene

The amines used to obtain the nitroso compounds have structures (IV) and (V) below.

(IV)

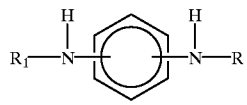

(V)

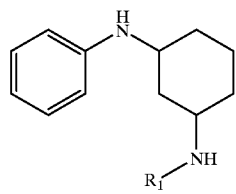

The reaction of nitrous acid with an amine is well known in the art. A specific example of the reaction using compound IV (above) is detailed in U.S. Pat. No. 5,869,717. An outline of this method is included here for completeness. Generally, the amine is reacted with nitrous acid at a temperature of about −10° C. to about 120° C. The nitrous acid can be added or it can be generated in situ by reacting sodium nitrite with hydrochloric acid. Further, in the case of a diamine, the amount of nitrous acid added will determine whether the mono or dinitroso compounds are obtained. However, even if a 1:1 stoichiometric amount of nitrous acid:amine is added, a mixture of the mono and dinitroso compounds may still be obtained.

In some cases it is preferred to add a thermal stabilizer to the mixture of inhibitors. A thermal stabilizer can inhibit the decomposition of the nitroso compound thus resulting in an inhibitor with greater thermal stability. What this means is that the temperature range over which the inhibitor can be used is extended. Specific examples where such a stabilizer is preferred are: 1) where the temperature in a distillation tower is too hot and 2) an accidental temperature excursion. These stabilizer can be selected from the group consisting of (IV)

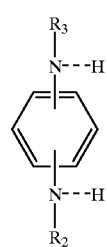

(V)

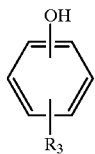

(VI)

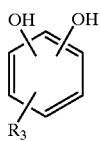

and mixtures thereof where $R_2$ is selected from the group consisting of hydrogen, phenyl, cyclohexyl and an alkyl group having from 1 to 18 carbon atoms, and $R_3$ is selected from the group consisting of hydrogen, cyclohexyl, an alkyl group having from 1 to 18 carbon atoms and an aromatic group having from 6 to 10 carbon atoms. Preferred stabilizers are those represented by structure (IV) and an especially preferred stabilizer has structure (IVA)

(IVA)

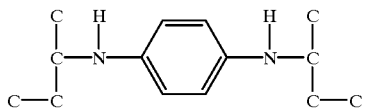

N,N'-di-2-butyl-1,4-diaminobenzene

Without wishing to be bound by any one particular theory, it appears that compounds such as (IVA) inhibit thermal decomposition by the following mechanism. It is first assumed that thermal decomposition of the nitroso compounds is triggered by cleavage of the nitroso group giving nitrous oxide (as evidenced by the evolution of a brown gas upon exposure to air). The nitrous oxide then catalyzes the further decomposition of the nitrosated inhibitor compound. One possible route for this further decomposition is the nitrous oxide induced cleavage of another nitrous oxide (autocatalysis).

Nitrous oxide is known to react with any primary or secondary amines such as phenylenediamines. Thus if phenylenediamine is present when nitrous oxide is formed, then the nitrous oxide will react with the amine and not be available to induce further cleavage of the nitroso compounds. However, phenylenediamines are not the only compounds with which the nitrous oxide can react. The phenolic compounds (structures V and VI) mentioned above can also react with the nitrous oxide. The amount of stabilizer necessary to increase the decomposition temperature is at least 0.0001 wt. %, but can vary from about 0.0001 to about 1 wt. % of the mixture of nitroso inhibitors.

In order to adequately prevent polymerization of the vinyl aromatic compounds, an effective amount of the mixture of nitroso compounds and dinitrophenolic compounds must be used. Usually the total effective amount of inhibitors varies from about 10 ppm to about 2 wt. %. The relative amount of each inhibitor in the mixture can vary widely but usually for the nitroso compound it is from about 1 ppm to about 50 wt. % with the dinitrophenolic compound and A optionally stabilizer making up the remainder of the mixture.

Having added the effective amount of inhibitor plus stabilizer to the feed containing the vinyl aromatic compound, the feed is distilled at a temperature of about 65° C. to about 150° C. in a standard distillation column. The distillation temperature can be controlled by adjusting the pressure in the column from about 0 kPa (0 psi) to about 165 kPa (24 psi) absolute. Further, the inhibitor and stabilizer mixture may be added to the vinyl aromatic compound in any convenient manner. Usually the mixture is added in liquid form by periodically or continuously adding the required amount to the inlet distillation feed. In this respect, if the inhibitor and/or stabilizer is a solid, it is dissolved in an appropriate solvent. Illustrative of the solvents which can be used are toluene, benzene, ethylbenzene, xylene, styrene etc. Preferred solvents are ethylbenzene or the starting amine which allows for easy separation from the purified vinyl aromatic compound.

The following examples are presented in illustration of the invention and are not intended as undue limitations in the generally broad scope of the invention as set out in the appended claims.

EXAMPLE 1

In a 3 L round bottom flask, thorn were placed 500 g of N,N'-di-2-butyl-1,4-diaminobenzene obtained from UOP and identified as UOP No. 5® and 700 g of hexanol. To this flask, which was held at a temperature between 20° C. and 40° C., there were added 460 g of concentrated hydrochloric acid (36 wt. % aqueous) drop-wise over a one-hour period. After this addition, the mixture was stirred for 10 minutes and then 325 g of sodium nitrite was added over a one-hour period while again maintaining the temperature between 20° C. and 40° C. After the addition was completed, the reaction mixture was neutralized to pH 7 by the addition of 84 g of sodium bicarbonate, which resulted in a dark brownish slurry. The slurry was filtered and the resulting solid product was washed with water and then ethanol to give an off-white to yellow crystalline solid identified as sample A. A sample of 2-sec-butyl-4,6-dinitrophenol was obtained from Aldrich Chemical Co., Inc.

EXAMPLE 2

The following test procedure was used to determine the ability of various samples to inhibit the polymerization of styrene. Five glass ampules were filled with 5 g of styrene and a given amount of a given sample. Four ampules were placed in an oil bath heated to 120° C. The fifth ampule was analyzed to give the initial amount of polymer. One ampule was removed at 1 hour increments and the contents filtered and weighed to determine an amount of polystyrene which was formed. In one test 200 wt. ppm of 2-sec-butyl-4,6-dinitrophenol (DNBP) was added to the styrene. In a second test, 200 wt. ppm of N,N'-di-2-butyl-N,N'-dinitroso-1,4-diaminobenzene (Dinitroso) was added to the styrene. In the third test 100 wt. ppm of each of the two inhibitors above was added to the styrene.

The amount of polystyrene formed for each test vs. time is presented in Table 1.

TABLE 1

Polymerization Inhibitor Activity of
Inhibitor Mixtures and Individual Components

| | WT. % POLYMER | | |
|---|---|---|---|
| HOURS | 200 wt. ppm DNBP | 200 wt. ppm Dinitroso | 100 + 100 wt ppm DNBP & Dinitroso |
| 1 | .4 | 0 | 0.3 |
| 2 | 1.3 | 0 | 0.3 |
| 3 | 3.5 | .4 | 1.2 |
| 4 | 8.5 | 4.5 | 3.5 |

Clearly the performance of the mixture was superior to that of DNBP. The mixture performed similarly to the 200 wt. ppm dosage of the Dinitroso inhibitor.

EXAMPLE 3

Styrene containing either 100 wt. ppm DNBP or 100 wt. ppm Dinitroso were tested using the procedure set forth in Example 2. The results of these tests are presented in Table 2.

TABLE 2

Comparison of Inhibitor Activity of DNBP and Dinitroso Compounds
at 100 wt. ppm Concentration.

| | wt. % Polymer | |
|---|---|---|
| Hours | 100 wt. ppm DNBP | 100 wt. ppm Dinitroso |
| 1 | 2.4 | 0 |
| 2 | 7.6 | 0.3 |
| 3 | 12.7 | 2.6 |
| 4 | 22.4 | 7.6 |

The results in Table 2 show that the Dinitroso inhibitor has superior activity versus DNBP at the 100 wt. ppm level. Comparing the results of Table 2 with Table 1 (100 wt. ppm DNBP+100 wt. ppm Dinitroso), it is observed that the mixture of the two inhibitors has better activity than what one would expect from a linear combination of the two components. That is, the mixture of two components results in a synergistic effect.

EXAMPLE 4

Three additional samples were tested using the procedure set forth in example 2 and the results are presented in Table 3.

TABLE 3

Effect of Relative Amounts of DNBP
and Dinitroso on Polymerization Inhibition.

| | WT. % POLYMER | | |
|---|---|---|---|
| HOURS | 500 wt. ppm DNBP 20 wt ppm Dinitroso | 250 wt. ppm DNBP 80 wt. ppm Dinitroso | 250 wt. ppm DNBP 40 wt. ppm Dinitroso |
| 1 | 0 | 0 | 0.2 |
| 2 | 0.4 | 0.1 | 0.5 |
| 3 | 0.8 | 0.1 | 1.8 |
| 4 | 1.7 | 0.7 | 2.6 |

The results in Table 3 show that even when DNBP is the major component (75% by weight) and the Dinitroso is the minor component, one obtains a synergistic effect (see Table 1) versus the individual components. The results also show that acceptable polymerization inhibition can be achieved while minimizing cost, by using the mixtures of the present invention.

We claim as our invention:

1. A process for inhibiting the polymerization of a vinyl aromatic compound during the distillation of the vinyl aromatic compound comprising adding to the compound an effective amount of a mixture of: 1) a nitroso compound selected from the group consisting of

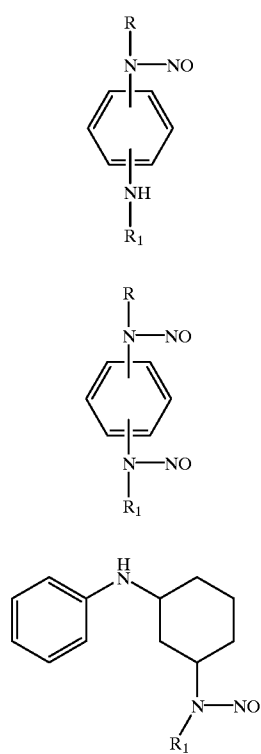

and mixtures thereof where R and $R_1$ are each independently hydrogen, cyclohexyl phenyl or an alkyl group having from 1 to 18 carbon atoms; and 2) a nitrophenol compound selected from the group consisting of dinitrophenol, dinitrocresol, 2-sec-butyl-4,6-dinitrophenol, and mixtures thereof.

2. The process of claim 1 where the nitroso compound is

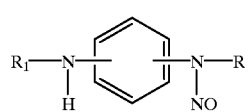

and the nitrophenol compound is selected from the group consisting of dinitrophenol, dinitrocresol, 2-sec-butyl-4,6-dinitrophenol, and mixtures thereof.

3. The process of claim 2 where the nitrophenol compound is dinitrocresol.

4. The process of claim 1 where the nitroso compound is

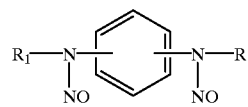

and the nitrophenol compound is selected from the group consisting of dinitrophenol, dinitrocresol, 2-sec-butyl-4,6-dinitrophenol, and mixtures thereof.

5. The process of claim 4 where the nitrophenol compound is dinitrocresol.

6. The process of claim 1 where the nitroso compounds are present in the mixture in an amount from about 1 ppm to about 50 wt. % of the mixture.

7. The process of claim 1 where the mixture concentration with respect to the vinyl aromatic compound varies from about 10 ppm to about 2 wt. %.

8. The process of claim 2 where the nitroso compound is (IA)

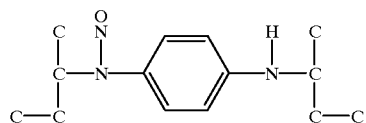

and the nitrophenol compound is dinitrocresol.

9. The process of claim 4 where the nitroso compound is (IIA)

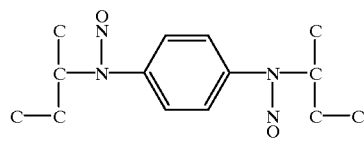

and the nitrophenol is dinitrocresol.

10. A process for inhibiting the polymerization of a vinyl aromatic compound comprising adding to the compound an effective amount of a mixture of: 1) a nitroso compound selected from the group consisting of (I)

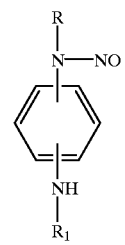

(II)

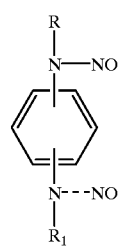

-continued

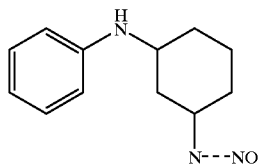
(III)

and mixtures thereof, where R and $R_1$ are each independently hydrogen, cyclohexyl, phenyl or an alkyl group having from 1 to 18 carbon atoms; 2) a nitrophenol compound selected from the group consisting of dinitrocresol, dinitrophenol, 2-sec-butyl-4,6-dinitrophenol, and mixtures thereof; and 3) a stabilizer selected from the group consisting of

(IV)

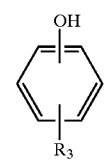
(V)

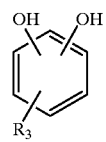
(VI)

and mixtures thereof, where $R_2$ is selected from the group consisting of hydrogen, phenyl, cyclohexyl and an alkyl group having from 1 to 18 carbon atoms, and $R_3$ is selected from the group consisting of hydrogen, cyclohexyl, an alkyl group having from 1 to 18 carbon atoms and an aromatic group having from 6 to 10 carbon atoms.

11. The process of claim 10 where the nitroso compound has structure (I), the nitrophenol compound is dinitrocresol and the stabilizer has structure (IV).

12. The nitroso process of claim 10 where the nitroso compound is N,N'-di-2-butyl-N-nitroso-1,4-diaminobenzene and the stabilizer is N,N'-di-2-butyl-1,4-diaminobenzene.

13. The process of claim 10 where the nitroso compound has structure (II), the nitrophenol compound is dinitrocresol and the stabilizer has structure (IV).

14. The process compound is N,N'di-2-butyl-N,N'-dinitroso-1,4diaminobenzene and the stabilizer is N,N'-di-2-butyl-1,4-diaminobenzene.

15. The process of claim 10 where the nitroso compound is a mixture of compounds having structures (I) and (II), the nitrophenol compound is dinitrocresol and the stabilizer has structure (IV).

16. The process of claim 15 where the nitroso compound is a mixture of N,N'-di-2-butyl-N,N'-dinitroso-1,4-diaminobenzene and N,N'-di-2-butyl-N-nitroso-1,4-diaminobenzene, the nitrophenol compound is dinitrocresol and the stabilizer is N,N'-di-2-butyl-1,4-diaminobenzene.

17. The process of claim 10 where the nitroso compounds are present in the mixture in an amount from about 1 ppm to about 50% of the mixture and the stabilizer is present in an amount from about 0.0001 to about 1 wt. % of the nitroso compounds.

18. The process of claim 10 where the nitrophenol compound is dinitrocresol.

* * * * *